United States Patent [19]

Mann et al.

[11] Patent Number: 4,808,167
[45] Date of Patent: Feb. 28, 1989

[54] MEDICATION INFUSION SYSTEM WITH DISPOSABLE PUMP/BATTERY CASSETTE

[75] Inventors: Alfred E. Mann, Los Angeles; Joseph H. Schulman, Granada Hills, both of Calif.

[73] Assignee: Pacesetter Infusion, Ltd., Sylmar, Calif.

[21] Appl. No.: 4,352

[22] Filed: Jan. 16, 1987

[51] Int. Cl.⁴ .............................................. A61M 1/00
[52] U.S. Cl. .................................... 604/151; 604/110; 128/DIG. 12
[58] Field of Search ................... 604/4, 30, 31, 65, 67, 604/80, 81, 110, 111, 123, 151-155; 128/DIG. 12, DIG. 13; 417/411, 476

[56] References Cited

U.S. PATENT DOCUMENTS

| | | | |
|---|---|---|---|
| 3,252,623 | 5/1966 | Corbin et al. | 222/59 |
| 3,543,662 | 12/1970 | Erlichman | 95/11 |
| 4,074,295 | 2/1978 | Kee | 354/145 |
| 4,142,524 | 3/1979 | Jassawalla | 604/123 |
| 4,256,437 | 3/1981 | Brown | 604/153 |
| 4,266,545 | 5/1981 | Moss | 604/110 |
| 4,324,473 | 4/1982 | Coughlan | 354/276 |
| 4,336,800 | 6/1982 | Giovanni | 128/DIG. 12 |
| 4,396,385 | 8/1983 | Kelly et al. | 128/DIG. 12 |
| 4,557,725 | 12/1985 | Heyne et al. | 604/151 |
| 4,634,430 | 1/1987 | Polaschegg | 604/4 |

FOREIGN PATENT DOCUMENTS 8500523  2/1985  PCT Int'l Appl. ................. 604/151

Primary Examiner—Stephen C. Pellegrino
Assistant Examiner—Ralph Lewis
Attorney, Agent, or Firm—Leslie S. Miller

[57] ABSTRACT

A disposable cassette for use with a main infusion pump unit is disclosed which contains both a disposable pump and a battery, thereby requiring the simultaneous replacement of both the pump and the battery. The controller contained in the main pump unit includes a timer which prevents the cassette from being used for longer than a predetermined time, which is substantially less than the life of the battery. An interlock prevents a cassette from being reinstalled following a single use.

19 Claims, 2 Drawing Sheets

MEDICATION INFUSION SYSTEM WITH DISPOSABLE PUMP/BATTERY CASSETTE

BACKGROUND OF THE INVENTION

Field of the Invention

The present invention relates generally to an electromechanical system for continuously infusing medication into a patient, and more particularly to such a system having a main pump unit onto which is installed a disposable cassette which includes the actual fluid pump used to precisely meter the amount of medication supplied, as well as a battery used as the primary power source for the medication infusion system.

In the past there have been two techniques used to deliver drugs which may not be orally ingested to a patient. The first large dosage at relatively infrequent intervals to the patient. This technique is not always satisfactory, particularly when the drug being administered is potentially lethal or has negative side effects when delivered in a large dosage. This problem results in smaller injections being given at more frequent intervals.

Alternatively, the second technique involves administering a continuous flow of medication to the patient through an IV bottle. Medication may also be delivered through an IV system with an injection being made into a complex maze of IV tubes, hoses, and other paraphernalia. As an alternative to these two techniques of administering medication to a patient, the recent addition of medication infusion pumps has come as a welcome improvement.

Infusion pumps are utilized to administer drugs to a patient in small, metered doses at frequent intervals or, alternatively, in the case of some devices, at a low but essentially continuous rate. Infusion pump therapy may be electronically controlled to deliver precise, metered doses at exactly determined intervals, thereby providing a beneficial gradual infusion of medication to the patient. In this manner, the infusion pump is able to mimic the natural process whereby chemical balances are maintained precisely by operating on a continuous time basis.

Such infusion pumps typically use as a power source a battery, which is contained inside the housing of the device. Most battery-powered infusion pumps use the battery as the power source for the electrical or electronic components used to control the infusion system in addition to using the battery to power the motor or other apparatus used to pump the medication being infused. It may be desirable to include an auxiliary battery such as a small lithium battery to power memory circuits during times when the main battery is being changed, thereby maintaining operating information stored in the solid state memory of the device.

In a battery operated infusion pump it may be appreciated that the state of charge of the battery is critical to ensure the continued operation of the device. In a hospital environment a nurse would have to remember to periodically recharge or change the battery in the device, making continued operation of the device absolutely dependent on changing the battery. Since a dead battery would result in the interruption of medication supplied to the patient, most infusion pumps have included some type of alarm to indicate when the battery must be changed. Since safety and reliability of medication infusion pumps are of primary importance, it is essential to have adequate safeguards in the design and operation of the device, and to avoid failure, even for relatively short periods of time.

An additional requirement has been imposed by the important design consideration of disposability. Since the portion of the device through which medication is pumped must be sterile, in most applications of infusion equipment some portions of the equipment are used only once and then disposed of, typically at regular intervals such as once daily. It is therefore desirable that the fluid pump portion of the infusion pump device be disposable, with the fluid pump being designed as an attachable cassette which is of inexpensive design, and which is easily installable onto the main pump unit. Any change in pump design must take this disposable nature of the pump portion into account.

It is desirable that the present invention ensure that the battery used to provide the primary power source for the infusion system be replaced at regular intervals, specifically at the same time the disposable pump cassette is replaced. Ensuring the simultaneous replacement of the pump cassette and the battery is therefore the primary objective of the present invention. The present invention must also retain the antiseptic nature of the disposable pump cassette while providing for the use of a fresh battery each time a new pump cassette is installed.

An incident advantage obtained in tying the replacement of the pump cassette to the replacement of the battery is that the disposal of the pump cassette will therefore be mandated with the installation of a replacement battery, thereby obviating the possibility of a disposable pump cassette being used beyond the period for which it was designed. The maximum period of use for the pump cassette will therefore be the period defined by the life of the battery. The installation of the pump cassette should therefore in the preferred embodiment involve the use of interlock means to prevent the pump cassette from being reused following its removal from the body of the infusion system after a single use of the cassette.

It is also desirable to retain a simple design to minimize the cost of construction of the disposable cassette, and to accomplish all these objects in a manner which will retain all of the advantages of reliability, durability, and safety of operation. All the advantages of the present invention will result in a superior medication infusion system having a number of advantages making the system a highly desirable alternative to systems presently available.

SUMMARY OF THE INVENTION

The disadvantages and limitations of the background art discussed above are overcome by the present invention. With this invention, the disposable pump cassette is constructed integrally with the battery which will furnish the primary power supply for operation of the infusion system. This invention imposes the advantageous requirement that the battery and the fluid pump be simultaneously and periodically replaced. The period of replacement of the pump cassette will be dictated by the life of the battery contained in the cassette, with the cassette being replaced at an interval determined by the life of the battery, the operation of the device, and a substantial margin of safety. The chances of error are reduced since a nurse or other person need no longer remember to periodically change the battery. In addition, the device has an obvious advantage over systems requiring the system to be plugged in to recharge a non-removable battery, in that it is always portable due to the replaceable battery design. Also, the time spent in recharging batteries is also eliminated, resulting in one less step in operating the device, an attractive prospect for use by medical professionals.

In the preferred embodiment, a fluid pump is mounted in one end of a plastic cassette housing, with the battery being mounted at the other end of the cassette housing. The cassette is snapped into place on the main pump housing, bringing the output of the prime mover into operational contact with the fluid pump. The prime mover may be any of a number of devices, such as a motor having a shaft output, a solenoid, or a hydraulic motor supplying varying pressure or vacuum.

Snapping the cassette into place also brings two contacts on the exterior of the cassette housing which are connected to the battery into contact with a pair of receiving contacts mounted on the main pump housing, thereby supplying power to the prime mover and associated electronics contained in the main pump housing. Snapping the cassette into place also causes a safety interlock mechanism to be operated, which safety mechanism will allow a cassette to be inserted into the pump housing only once. This interlock may be either of a mechanical or electrical nature, with several possible embodiments being suggested in the detailed description below.

The present invention also includes a timer feature which is used to ensure the cassette is replaced prior to battery failure. The device may be disabled after a preset period of time following installation of a new cassette. Another approach of the preferred embodiment is to provide additional checks which are used to disable operation of the device unless a new cassette is installed. If the prime mover does not operate for an extended period, or if battery voltage falls off, the device is disabled. Appropriate alarms or signals may be used to indicate the occurrence of such conditions.

The present invention therefore represents a solution to the problems discussed above in that a battery is packaged integrally with the disposable fluid pump. A fresh battery is always present when a new cassette is installed, and the cassette and battery are usable only once, therefore preventing reuse of a cassette which may be contaminated and a battery which may be less than fresh. Tying the battery and the fluid pump together also has the benefit of making periodic replacement of the pump mandatory.

Built in safeguards prevent the cassette from being used beyond a period in which an acceptable battery level is assured, and also ensure that the device will not be usable after an extended period of disuse. The present invention therefore represents a highly desirable improvement in the art, encompassing the advantages enumerated above with substantially no relative disadvantage.

DESCRIPTION OF THE DRAWINGS

These and other advantages of the present invention are best understood with reference to the drawings, in which.

DETAILED DESCRIPTION OF THE PREFERRED EMBODIMENT

Figure 1:
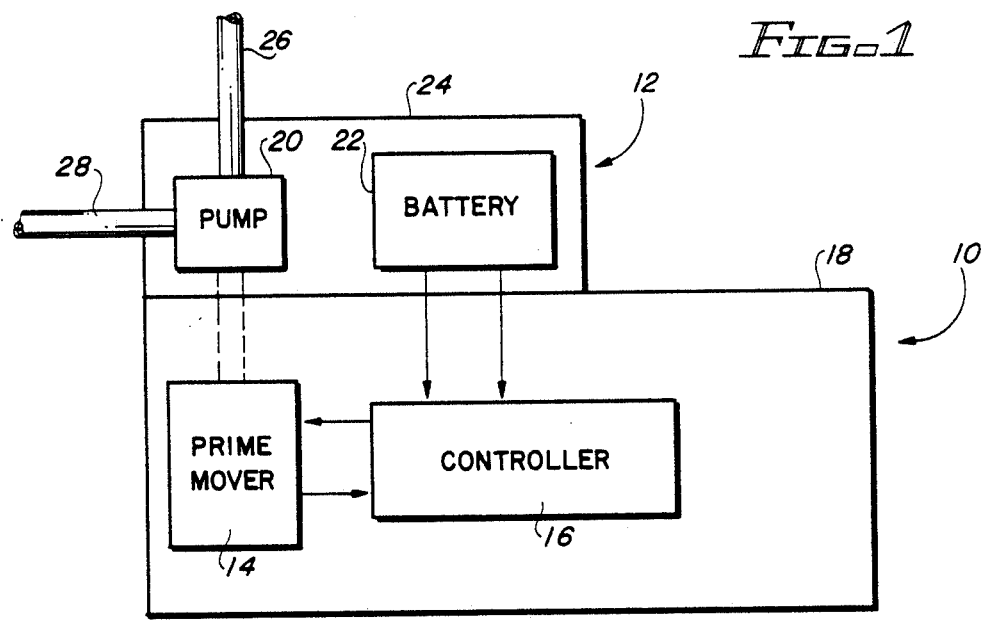
FIG. 1 is a highly schematic drawing of an infusion system embodying the present invention and illustrating the pump and battery contained in a single disposable cassette.

The present invention, which is schematically illustrated in its simplest form in FIG. 1, has two main components- a main pump unit 10 and a disposable cassette 12. The main pump unit 10 includes a prime mover 14 which functions to provide motive power, and a controller portion 16, both of which are mounted in a main pump housing 18. The cassette 12 has a pump 20 and a battery 22 mounted within a cassette housing 24. The pumping capacity of the pump 20 may vary, according to the rate requirements of the pump 20 for a particular fluid to be pumped. Different cassettes 12 may be manufactured with different capacity pumps 20 for use with a variety of therapeutic fluids.

Likewise, it may be desirable to use a different size battery 22 for different capacity pumps 20. If large quantities of fluid are to be pumped, a larger battery 22 may be required. The battery 22 for a high capacity pump 20 may be larger than that shown in the drawings, and the battery 22 could extend down one side of the main pump unit 10, since the cassette 12 is installed at the edge of the main pump unit 10.

When the cassette 12 is attached to the main pump unit 10, the battery 22 is connected to furnish electrical power to the controller 16 and the prime mover 14, and the pump 20 is placed in position to be driven by the prime mover 14. The pump 20 has an inlet 26 which is used to supply the pump 20 with a therapeutic fluid from a fluid source (not shown). Likewise, the pump 20 has an outlet 28 through which the therapeutic fluid is pumped in precisely metered quantities, with fluid leaving the pump 20 through the outlet 28 being directed eventually to a patient (not shown).

The prime mover 14 may be any of a number of drive mechanisms, including but not limited to an electric motor, a stepper motor, a solenoid apparatus, or a hydraulic motor providing a variable pressure or vacuum. The pump 20 will be adapted to be driven by the prime mover 14, as those skilled in the art will appreciate. The specific types of prime mover 14 and pump 20 used in not particularly pertinent to the present invention, inasmuch as the present invention works equally well with any drive/pump scheme.

The controller 16 operates the prime mover 14 according to programmed instructions, to thereby cause the pump 20 to pump specific amounts of therapeutic fluid at specific times. It is apparent that the present invention as thus far disclosed has particular advantages over the art, due to the fact that the pump 20 and the battery 22 are contained in a single disposable cassette 12. A new pump 20 may not be installed without simultaneously installing a new battery 22. This eliminates the possibility of system failure due to medical personnel changing a disposable pump but failing to install new batteries in the device.

The use of a new battery 22 also necessitates the use of a new pump 20, which is an incidental advantage obtained by the system of the present invention. Since the battery 22 has a relatively well defined lifetime and must be periodically replaced in order for the system to operate, the pump 20 will therefore also be periodically replaced. Other features and embodiments of the present invention require a more detailed example than that depicted in FIG. 1 and discussed to this point.

Figure 2:
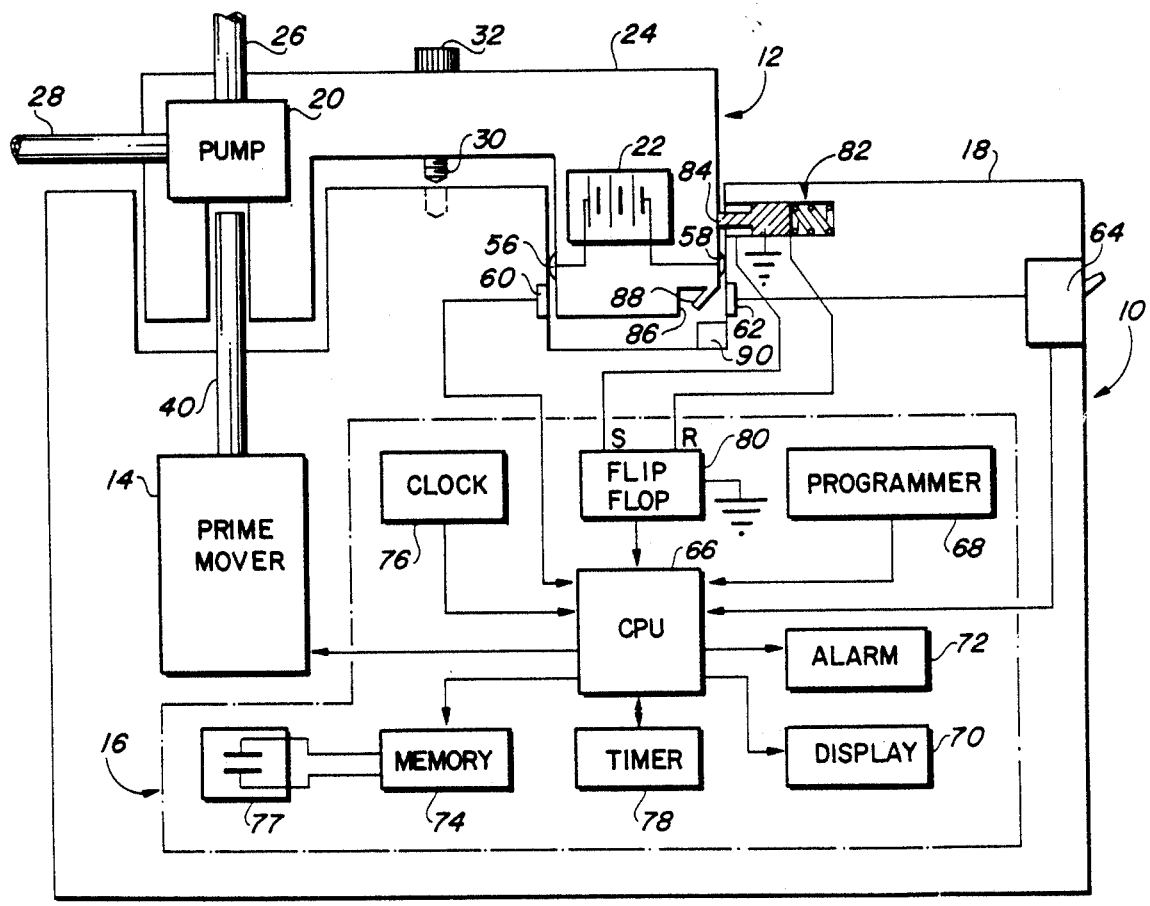
FIG. 2 is a schematic representation of an implementation of the infusion system of FIG. 1 using a mechanical interlock to prevent reuse of the cassette.

Referring now to FIG. 2, an example of one possible configuration utilizing the present invention is shown. The cassette 12 has the pump 20 at one end and the battery 22 at the other end, with the portions of the cassette 12 in which the pump 20 and the battery 22 are contained fitting into recesses in the main pump unit 10 to help provide a strong attachment between the cassette 12 and the main pump unit 10. The cassette 12 may be removably held in place by a connecting screw 30 having a knob 32 at the end of the screw 30 extending from the cassette 12. After placing the cassette 12 into position on the main pump unit 10, the screw 30 is turned to securely fasten the cassette 12 to the main pump unit 10.

Of course, those skilled in the art will immediately realize that there are a number of different ways to removable secure the cassette 12 to the main pump unit 10. For example, plastic clips (not shown) made as an integral part of the cassette housing 24 may be used, with the plastic clips fitting into mating surfaces (not shown) in the main pump housing 18. There are numerous other alternatives, none of which depart from the spirit of the invention.

The cassette housing 24 holds the pump 20 and the battery 22 in an integral package, and may do so in various ways. The cassette housing 24 may be two or more pieces of molded plastic, for example, or it may be a rigid portion cast or molded around the battery 22 and the pump 20. In any event, the pump 20 and the battery 22 are contained in the cassette housing 24 so that the cassette 12 as a unit must be removed and disposed of, thereby making the simultaneous replacement of the pump 20 and the battery 22 a necessity.

This requirement ensures that the pump 20 and associated portions having contact with the therapeutic fluid will be replaced and a fresh battery 22 will be provided each time the cassette 12 is replaced. Both the reliability and the antiseptic nature of the infusion system are therefore enhanced. As is apparent, the battery 22 is a non-rechargeable battery, since the cassette 12 is not to be reused. Since under usual operating circumstances the pump 20 would require replacement before the battery 22 is exhausted, it is apparent that a reserve of energy representing a substantial margin of safety exists.

In FIG. 2 the prime mover 14 is schematically shown to be connected to the pump 20 by a mechanical drive connection 40. These components are shown in highly schematic fashion since any of a number of different drive, pump, and connection means may be used without affecting the nature of the present invention. Various drive schemes are well known in the art, and any of these schemes could be adapted for use with the present invention.

Figure 5:
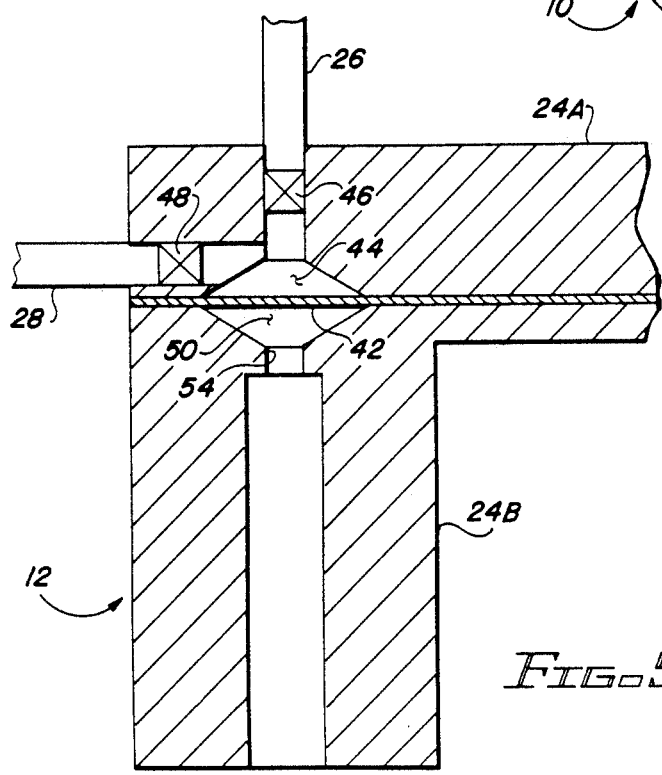
FIG. 5 is a cutaway view of a simple pump driven by pressure or vacuum.

One possible type of pump 20 is illustrated in FIG. 5, which has the various components mounted between two halves of a cassette housing 24A and 24B. The pump 20 illustrated in FIG. 5 is one which would be driven by a hydraulic motor (not shown), which would supply alternating air pressure and vacuum. Two chambers separated by a diaphragm 42 located between the two halves of the cassette housing 24A and 24B form the working part of the pump 20.

An upper or pumping chamber 44 in one of the cassette housing halves 24A is the chamber in which the therapeutic fluid will be present. The therapeutic fluid enters the pumping chamber 44 through a one-way inlet valve 46 which is supplied with the therapeutic fluid from the inlet 26. The one-way inlet valve 46 permits fluid flow only from the inlet 26 into the pumping chamber 44. The therapeutic fluid leaves the pumping chamber 44 through a one-way outlet valve 48 which communicates with the outlet 28, through which it will be supplied to a patient. The one-way outlet valve 48 likewise permits fluid flow in one direction only, from the pumping chamber 44 to the outlet 28.

A lower or drive chamber 50 is located in the other half of the cassette housing 24B, on the other side of the diaphragm 42 from the pumping chamber 44. The drive chamber 50 is supplied with pressure and vacuum from the hydraulic motor (not shown) contained in the main pump unit 10 (FIG. 2). An 0-ring 52 is located about a channel 54 in the other half of the cassette housing 24B, which 0-ring is used to provide a seal between portions of the mechanical drive connection 40 (FIG. 2) connecting to the channel 54.

By alternately supplying pressure to the drive chamber 50, fluid will be pumped by the pumping chamber 44 from the inlet 26 to the outlet 28. The description of the pump 20 is given by way of example only, and is not intended as a limitation of any kind on the present invention. In fact, a number of different types of pump 20 could be used equally well, such as piston type pumps, rotary pumps, cam actuated pumps, and double acting pumps.

Referring again to FIG. 2, the electrical connection of the disposable battery 22 contained in the cassette 12 to the controller 16 located in the main pump unit 10 is illustrated. The two poles of the battery 22 are connected inside the cassette 12 to two battery terminals 56, 58 which are mounted on the outside of the cassette housing 24, on portions of the cassette housing 24 contacting or closely adjacent to the main pump housing 18. In the embodiment illustrated in FIG. 2, the battery terminals 56, 58 are mounted on a portion of the cassette housing 24 extending into a recess in the main pump unit 10.

There are two corresponding electrical contacts 60, 62 mounted on the exterior of the main pump housing 18, which contacts 60, 62 will be in electrical communication with the battery terminals 56, 58, respectively, when the cassette 12 is mounted onto the main pump unit 10. In the preferred embodiment illustrated in FIG. 2, the battery terminals 56, 58 protrude from the cassette housing 24, and the electrical contacts 60, 62 are essentially flush with the surface of the main pump housing 18. Of course other designs may be utilized, and one variation would be to have a snap type fit or spring loading between the battery terminals 56, 58 and the electrical contacts 60, 62, with the snap fit being used to help retain the cassette 12 in position on the main pump unit 10.

Electrical power is thus supplied from the battery 22 to the controller 16, with a switch 64 typically being included in the electrical path between the battery 22 and the controller 16. The controller 16 has several components likely to be included illustrated schematically in FIG. 2, with a central processing unit (CPU) 66 representing the heart of any electronic design for the controller 16. The CPU 66 will control the application of power to the prime mover 14 to cause the therapeutic fluid to be pumped at specific selected rates or in specific amounts and at specific selected times.

A programmer 68 is used to set or enter the various parameters of operation of the system, which parameters are supplied to the CPU 66. The programmer 68 may be a keyboard or other manual input device, or it may include either alternatively or in addition to the manual input device receiving facilities for obtaining programming information from an external programming unit (not shown). Typical information entered through the programmer may include various times for various operations to take place, the rate of operations (which would set pump rate), and the lengths of such operations.

A display 70 may be provided to provide a visual indication of information entered through the programmer 68, which display 70 receives output signals from the CPU 66. The display 70 may also be used to provide information on the operation of the system during operation of the system, in which case the display 70 would be of a low power type, such as an LCD display. An audible alarm 72 may also be used to indicate successful entry of information, errors in entering the information, etc. The CPU 66 is able to store and access information from a memory 74, and is supplied with signals from a clock 76. The memory 74 may also be reset through the programmer 68 for use with a new patient, but will be preserved for the same patient even when the device is reprogrammed for different medications, rates, or times.

An auxiliary battery 77, typically a long life lithium or similar battery, is used to sustain the memory 74 and the CPU 66 during times when a new cassette 12 is being installed and no main power source is present. Alternately, a low-leakage, high value capacitor may be used instead of the auxiliary battery 77, with such a capacitor being capable of powering the memory 74 for at least a week or so. In this case, the battery 22 is used to recharge the low-leakage high value capacitor. Note that the battery 22 could also be used to recharge the auxiliary battery 77. A timer 78 supplies information indicative of various elapsed times to the CPU 66.

The timer 78 may be started upon installation of the cassette 12 and a fresh battery 22, with a specific time interval embodied in the device as a maximum operating time interval without a cassette change. For example, three days could be set as the maximum operational period without a new cassette 12 being installed. This time period would always include a substantial margin of safety, with the system being assumed to be operating at a maximum operational power draw for the time period. After this time period is reached, the system could be shut down, with no further power being supplied to drive the prime mover 14. At this time, a visual indication could be presented on the display 70, and an audible alarm could be emitted from the alarm 72. Alternatively, the system could drive a display and/or alarm at a central nursing station in a hospital environment.

Another approach to the shutdown of the system when the battery 22 is not replaced is the monitoring of the voltage produced by the battery 22 When the battery 22 voltage falls to a predetermined level, the alarm 72 is sounded. When the battery 22 voltage falls to a second lower predetermined level, the system is shut down, with the battery 22 being used only to help maintain the memory 74.

An additional feature which may be included in the system is the incorporation of a system shutdown for other reasons, such as a system failure or the absence of operation of the prime mover 14 over a shorter period of time, such as a two day period. Under such circumstances, the controller 16 would be disabled until a new cassette 12 is installed.

While the timing operations could be controlled by the use of an initial startup sequence at which time the timer 78 is reset and started, the preferred embodiment shown in FIG. 2 uses a flip-flop 80 and a three-way switch 82 to perform this function. When no cassette 12 is installed, the switch 82 will toggle the reset of the flip-flop 80, to indicate to the CPU 66 that the cassette 12 has been removed. When a cassette 12 is installed the switch 82 will toggle the set of the flip-flop 80, to cause the timer 78 to begin the three day sequence. It will be realized by those skilled in the art that many alternatives to the described use of the flip-flop 80 exist, all of which are acceptable and do not depart from the present invention.

Finally, another aspect which may be incorporated into the present invention involves the use of an interlock to prevent the reuse of a cassette 12. In a hospital when trained professionals are maintaining the system, the need for such an interlock may be minimal, but for home use of the system such an interlock is highly desirable. Interlocks may be either electrical or mechanical, and a mechanical interlock is illustrated in FIG. 2. This interlock utilizes the switch 82, which is spring loaded to bias the pin 84 of the switch 82 to extend out of the main pump housing 18. The cassette housing 24 has a lower corner with a notch 86 therein, with a sloped link 88 extending at an angle across the notch 86. The sloped link 88 permits the cassette 12 to be inserted past the pin 84, with the angled surface of the sloped link 88 sliding the pin 84 back into the switch 82.

After the pin 84 is pushed in and the cassette 12 is lowered further towards its position on the main pump unit 10, the sloped link 88 will be met by a bumper 90 protruding from the main pump housing 18 and sized to fit within the notch 86 when the cassette 12 is attached to the main pump unit 10. The bumper 90 will break off the sloped link 88, or alternately bend it back so as to permanently deform it. It is thus apparent that if the cassette 12 is removed from the main pump unit 10, it will not be able to be replaced since the pin 84 of the switch 82 will hang up in the notch 86, since the sloped link 88 is either broken off or bent back. After a cassette 12 has been removed, it will therefore be necessary to use a new cassette 12.

Figure 3:
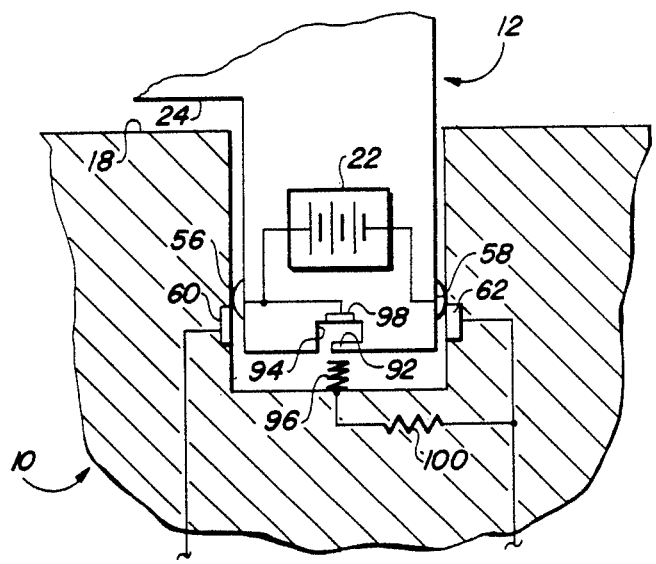
FIG. 3 is an alternate embodiment to the mechanical interlock of FIG. 2 in which an electrical interlock is used.
Figure 4:
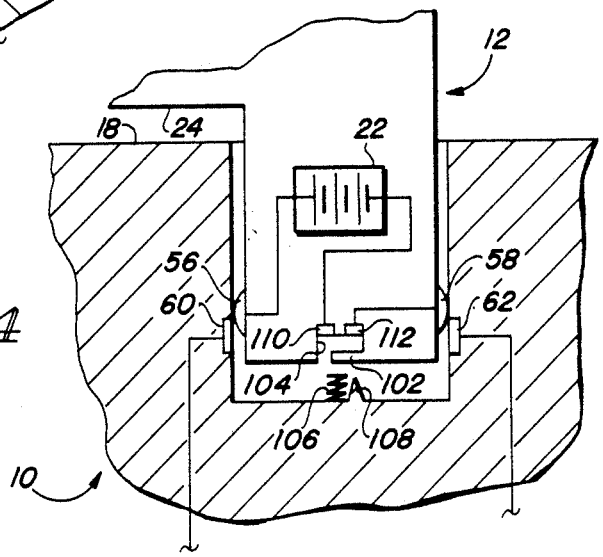
FIG. 4 is an additional alternate embodiment illustrating a second configuration for an electrical interlock.

Alternate embodiments using an electrical interlock are illustrated in FIG. 3 and 4. In FIG. 3, on the bottom of the portion of the cassette 12 containing the battery 22 is a small, readily breakable link 92 covering a small recess 94. A spring 96, which is made of conductive material, is mounted in the portion of the main pump unit 10 receiving the portion of the cassette 12 containing the battery 22 will act to break the link 92, which is made of nonconductive material. The link 92 will be forced against the top of the recess 94, insulating the spring from a contact 98 contained in the top side of the recess 94.

When the cassette 12 is removed and subsequently reinstalled, the link 92 will no longer remain to insulate the spring 96, which will touch the contact 98. This completes a circuit including a resistor 100 connected between the spring 96 and the electrical contact 58, and discharges the battery 22. The reuse of the cassette 12 is thereby effectively prevented. The resistor 100 is small enough to discharge the battery 22 relatively quickly, but large enough to prevent overheating caused by the discharging of the battery 22 and to have adequate heat dissipating capacity.

Another electrical interlock is illustrated in FIG. 4, which again has a breakable link 102 disposed on the bottom of the portion of the cassette 12 containing the battery 22, with the link 102 covering a recess 104. This time, however, the link 102 is made of a conductive material. A spring 106 similar to the spring 96 of FIG. 3 is again used, with the spring 106 being made of nonconductive or insulated material. A small wedge 108 mounted on the main pump unit 10 next to the spring 106, which wedge 108 breaks the link 102 as the cassette 10 is attached to the main pump unit 10, and the spring 106 forces the link 102 against the top of the recess 104.

Two contacts 110, 112 are located in the top of the recess 104, with the contact 110 being attached to the battery 22 and the contact 112 being attached to the battery terminal 58 (The battery terminal 58 is no longer directly connected to the battery 22. The link 102 will close the circuit and operate the system when the cassette 12 is attached to the main pump unit 10 for the first time. When the cassette 12 is removed, the link 102 will no longer be in the recess 104, and the nonconductive spring 106 will not complete the circuit. The system will thus not receive any power if the cassette 12 is installed more than once.

It may therefore be appreciated that the present invention presents a system having a disposable cassette containing both a pump and a battery. The system has an interlock preventing a cassette which is removed from being reinstalled. The system further requires that the cassette be changed periodically, otherwise the system is shut down and an alarm is given. The result of the integration of the pump and the battery is that both must be periodically changed, and the system thus prevents too long a use of both the disposable pump and the battery, thereby eliminating problems attending overly extended use of either the pump or the battery.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications, and alterations should therefore be seen as within the scope of the present invention.

What is claimed is:

1. A medication infusion system for infusion system for infusing fluid into a living body, comprising:
   a disposable fluid pump having an inlet to which aid fluid is supplied for ma source, and an outlet form which said fluid is pumped in precisely metered amounts at preselected times;
   a prime mover for driving said disposable fluid pump;
   means for coupling an output of said prime mover to drive said fluid pump;
   an electronic controller for controlling the operation of said prime mover to cause said disposable fluid pump to pump said precisely metered amounts at said preselected times;
   main pump housing means for containing said prime mover and said electronic controller in an assembly defining a main pump unit;
   a battery for powering at least one of said prime mover and said electronic controller, said battery being attached to and disposable with said disposable fluid pump;
   cassette housing means for containing said disposable fluid pump and said battery in an integral package defining a disposable cassette, said disposable cassette for removable attachment to said main pump unit;
   means interacting between said cassette and said main pump housing for preventing reuse of said disposable cassette after initial detachment form said main pump unit; and
   means for connecting said battery to provide electrical power to at least one component contained in said main pump unit.

2. A medication infusion system as defined in claim 1, wherein said connecting means comprises:
   electrical battery terminals located on said disposable cassette and engaging in sliding contact with electrical contacts located on said main pump housing when said disposable cassette is attached to said main pump unit.

3. A medication infusion system as defined in claim 1, wherein said connecting means is usable only once to prevent reuse of said disposable cassette.

4. A medication infusion system as defined in claim 1, wherein said preventing means comprises:
   a spring loaded switch having a pin biased to extend out of said main pump housing;
   a notch in a lower corner of said cassette housing;
   a sloped link extending at an angle across said notch, which sloped link permits said disposable cassette to be inserted past said pin, the angled surface of said sloped link sliding said pin back into said switch; and
   a bumper protruding from said main pump housing and sized to fit within said notch when said disposable cassette is attached to said main pump unit after said pin is slid back into said switch, said bumper either breaking off said sloped link, or bending it back so as to permanently deform it, thus preventing reinsertion of said disposable cassette since said pin will hang up in said notch upon reinsertion of said disposable cassette since said sloped link is either broken off or bent back.

5. A medication infusion system as defined in claim 4, wherein said switch is used to detect the presence of said disposable cassette and causes said system to be reset.

6. A medication infusion system as defined in claim 1, wherein said preventing means comprises:
   means for quickly discharging said battery upon reuse of said disposable cassette to disable said system, thereby preventing said battery from powering power to operate said system.

7. A medication infusion system as defined in claim 1, wherein said cassette housing is a rigid portion cast or molded around said battery and said disposable pump.

8. A medication infusion system as defined in claim 1, additionally comprising:
   means for limiting the use of said system in response to the occurrence of specific circumstances.

9. A medication infusion system as defined in claim 8, wherein said limiting means comprises:

means for limiting the time said system will operate after the installation of a new disposable cassette without the replacement of that cassette, thereby shutting the system down if the disposable cassette is not replaced within a preset maximum time period.

10. A medication infusion system as defined in claim 8, wherein said limiting means comprises:

means for preventing further use of said system if said fluid pump has not operated to pump said fluid for a predetermined maximum period of time.

11. A medication infusion system s defined in claim 1, wherein said electronic controller comprises:

a central Processing Unit (CPU) for controlling the application of power to said prime mover to cause said fluid to be pumped by aid fluid pump;

a programmer for setting the various parameters of operation of said system, which parameters are supplied to said CPU;

a display for providing a visual indication of information entered through said programmer and for providing information on the operation of said system;

a memory for storing information which may be accessed by said CPU;

a long life power source for sustaining said memory and said CPU during times when a new disposable cassette is being installed and no main power source is present.

12. A medication infusion system as defined in claim 11, wherein said long life power source is a battery.

13. A medication infusion system as defined in claim 11, wherein said long life power source is a low-leakage long life capacitor.

14. A medication infusion system as defined in claim 1, additionally comprising:

means for monitoring said battery;

means, responsive to said monitoring means, for providing an alarm if the level of said battery falls below a first predetermined level.

15. A medication infusion system as defined in claim 14, wherein said providing means will cause said system to cease pumping fluid if the level of said battery falls below a second predetermined level which is lower than said first predetermined level.

16. A medication infusion system, comprising:

a fluid pump having an input to which said fluid is supplied from a source, and an outlet from which said fluid is pumped;

a battery for providing electrical power for said medication infusion system;

means for connecting said battery to provide electrical power to at least one component contained in said main pump unit;

cassette housing means for containing said fluid pump and said battery in an integral package defining a disposable cassette, said disposable cassette for removable attachment to a main pump unit, said disposable cassette being disposable after one use;

a prime mover for providing a mechanical output used to drive said fluid pump;

means for coupling an output of said prime mover to drive said fluid pump;

an electronic controller for driving said prime mover;

main pump housing means for containing said prime mover and said electronic controller in an assembly defining said main pump unit; and means interacting between said cassette and said main pump housing, for preventing reuse of said disposable cassette after initial detachment from said main pump unit.

17. A medication infusion system as defined in claim 16, further comprising:

means to ensure said disposable cassette is not reused after detachment form said main pump unit.

18. A medication infusion system, comprising:

a prime mover for providing a mechanical output;

an electronic controller for driving said prime mover;

main pump housing means for containing said prime mover and said electronic controller in an assembly defining a main pump unit;

a disposable fluid pump having an input to which said fluid is supplied from a source, and an outlet from which said fluid is pumped in precisely metered amounts at preselected times;

means for coupling said mechanical output of said prime mover to drive said disposable fluid pump;

a disposable battery for providing electrical power for said prime mover and said controller;

means for connecting said battery to provide electrical power to at least one component contained in said main pump unit;

cassette housing means for containing said disposable fluid pump and said disposable battery in an integral package defining a disposable cassette, said disposable cassette for removable attachment to said main pump unit, said disposable cassette being disposable after one use: and means interacting between said cassette and said main pump housing, for preventing reuse of said disposable cassette after initial detachment from said main pump unit.

19. A method of providing a flow of medical fluid to a living body, comprising:

providing a disposable fluid pump having an inlet to which said fluid is supplied from a source, and an outlet from which said fluid is pumped in precisely metered amounts at preselected times;

driving said disposable fluid pump with a prime mover, an output of said prime mover being coupled to drive said disposable fluid pump;

controlling the operation of said prime mover with an electronic controller to cause said disposable fluid pump to pump said precisely metered amounts at said preselected times;

installing said prime mover and said electronic controller in an assembly defining a main pump unit;

powering at least one of said prime mover and said electronic controller with a battery, said battery being attached to and disposable with said disposable fluid pump, and connected to provide electrical power to at least one component contained in said main pump unit;

installing said disposable fluid pump and said battery in an integral package defining a disposable cassette, said disposable cassette for removable attachment to said main pump unit; and preventing reuse of said disposable cassette after initial detachment from said main pump unit.

* * * * *